(12) United States Patent
Kobayashi

(10) Patent No.: US 7,001,330 B2
(45) Date of Patent: Feb. 21, 2006

(54) ENDOSCOPE SYSTEM INCLUDING SYSTEM FOR OBTAINING USAGE CONDITION

(75) Inventor: Hiroyuki Kobayashi, Saitama-ken (JP)

(73) Assignee: PENTAX Corporation, Tokyo (JP)

( * ) Notice: Subject to any disclaimer, the term of this patent is extended or adjusted under 35 U.S.C. 154(b) by 0 days.

(21) Appl. No.: 10/157,145

(22) Filed: May 30, 2002

(65) Prior Publication Data
US 2002/0188173 A1 Dec. 12, 2002

(30) Foreign Application Priority Data
May 30, 2001 (JP) .............................. 2001-162090

(51) Int. Cl.
*A61B 1/04* (2006.01)
(52) U.S. Cl. ..................................... 600/118; 600/117
(58) Field of Classification Search ................ 600/117, 600/118, 103, 109
See application file for complete search history.

(56) References Cited

U.S. PATENT DOCUMENTS

| | | | | |
|---|---|---|---|---|
| 4,862,872 A | * | 9/1989 | Yabe et al. .................. | 600/133 |
| 4,996,975 A | * | 3/1991 | Nakamura .................. | 600/118 |
| 5,359,993 A | * | 11/1994 | Slater et al. ................. | 600/133 |
| 5,830,121 A | * | 11/1998 | Enomoto et al. ............ | 600/117 |
| 5,871,439 A | * | 2/1999 | Takahashi et al. .......... | 600/118 |
| 5,967,969 A | * | 10/1999 | Enomoto et al. ........... | 600/117 |
| 6,166,538 A | * | 12/2000 | D'Alfonso .................. | 324/228 |
| 6,322,496 B1 | * | 11/2001 | Iida et al. .................... | 600/118 |
| 6,364,827 B1 | * | 4/2002 | Irion et al. .................. | 600/118 |
| 6,368,270 B1 | * | 4/2002 | Takami ....................... | 600/178 |
| 6,413,210 B1 | * | 7/2002 | Enomoto .................... | 600/178 |
| 6,436,032 B1 | * | 8/2002 | Eto et al. .................... | 600/117 |
| 6,638,212 B1 | * | 10/2003 | Oshima ...................... | 600/109 |
| 2001/0041825 A1 | * | 11/2001 | Shibata et al. .............. | 600/118 |

* cited by examiner

Primary Examiner—John P. Leubecker
(74) Attorney, Agent, or Firm—Greenblum & Bernstein, P.L.C.

(57) ABSTRACT

There is provided an electronic endoscope system, which is provided with an electronic endoscope, and an endoscope processor to which the electronic endoscope is detachably connected. The electronic endoscope system is further provided with a usage status monitoring system which monitors a usage status of the electronic endoscope system and outputs status data, and a usage condition obtaining system which obtains a usage condition of the electronic endoscope system based on the status data. The usage condition obtaining system updates the usage condition based on the status data successively output by the usage status monitoring system.

7 Claims, 11 Drawing Sheets

ENDOSCOPE SYSTEM INCLUDING SYSTEM FOR OBTAINING USAGE CONDITION

BACKGROUND OF THE INVENTION

The present invention relates to an electronic endoscope system for automatically collecting information regarding usage of an electronic endoscope system.

The conventional electronic endoscope system typically includes an electronic endoscope that is provided with an image capturing element such as a CCD (Charge Coupled Device) and an endoscope processor that processes an image signal outputted by the image capturing element and transmits the processed image signal to an outputting device such as a display, video printer or the like.

There are various kinds of electronic endoscopes. The various kinds of electronic endoscopes are selectively and detachably attached to the endoscope processor for endoscopic observation/operation.

Generally, an endoscope system including one endoscope processor and at least one electronic endoscope is very expensive. Therefore, in many cases, the electronic endoscope system is used on rental basis.

A rental fee is typically determined based on a usage condition of the endoscope system within a certain time period (for example, a month). However, the conventional endoscope system does not automatically collect information regarding usage of the electronic endoscope system.

Conventionally, a service person periodically visits a facility or a clinic where the electronic endoscope system is implemented to check the usage condition. Typically, a user at the facility etc. informs the service person of the number of patient charts which correspond to the number of usages of the electronic endoscope system. Then, the service person determines the renting fee based on the number of usages, for example, by multiplying the number of usages by a predetermined coefficient.

In the above-described case, the user is required to preliminarily select the patient charts corresponding to, the usage of the electronic endoscope system, which is very troublesome for the user.

In addition, in some cases, the number of the patient charts does not reflect the usage condition accurately since the number of times the electronic endoscope system is used for one observation/operation may not be constant.

Accordingly, an electronic endoscope system or a method which provides accurate information indicative of the usage condition of the electronic endoscope system has been desired.

SUMMARY OF THE INVENTION

The present invention is advantageous in that it provides an improved electronic endoscope system and/or a method which enables collection of accurate information indicative of the usage condition of the electronic endoscope system.

According to an aspect of the invention, there is provided an electronic endoscope system, which is provided with an electronic endoscope, and an endoscope processor to which the electronic endoscope is detachably connected. The electronic endoscope system is further provided with a usage status monitoring system which monitors a usage status of the electronic endoscope system and outputs status data, and a usage condition obtaining system which obtains a usage condition of the electronic endoscope system based on the status data. The usage condition obtaining system updates the usage condition based on the status data successively output by the usage status monitoring system.

With this configuration, the accurate information indicative of the usage condition of the electronic endoscope system can be automatically collected.

Optionally, the usage condition obtaining system may include a first memory in which the usage condition is stored.

Still optionally, the usage status monitoring system may include a detecting system which determines whether the electronic endoscope is connected to the endoscope processor. In this case, the status data includes detection results of the detecting system.

In a particular case, the usage condition obtaining system may include a counting system which counts the number of times by which the electronic endoscope is connected to the endoscope processor based on the detection result output by the detecting system. In this case, the usage condition includes the number of times by which the electronic endoscope is connected to the endoscope processor.

Alternatively or optionally, the usage condition obtaining system may include a timer, and a time measuring system which measures a total time period for which the electronic endoscope is connected to the endoscope processor using the timer based on the detection result output by the detecting system. In this case, the usage condition includes the total time period.

In a particular case, the usage status monitoring system may be configured to detect the type of the electronic endoscope connected to the endoscope processor. In this case, the usage condition obtaining system may categorize the usage condition by the type of the electronic endoscope.

In some embodiments, the electronic endoscope may include a second memory in which a manufacturing number thereof is stored. In this case, the detecting system may detect the type of the electronic endoscope by reading the manufacturing number from the second memory.

Optionally, the usage condition obtaining system may include a reset system which resets the usage condition stored in the first memory.

In a particular case, the usage condition obtaining system may be incorporated into the endoscope processor.

Still optionally, the electronic endoscope system may include an external device which is connected to the endoscope processor. In this case, the usage condition obtaining system may be incorporated into the external device.

In a particular case, the usage condition obtaining system may be incorporated into the electronic endoscope.

In some embodiments, the endoscope processor may include a light source which emits light for illuminating an object to be observed to a light guide provided in the electronic endoscope, the usage status monitoring system may include a detecting system which determines whether the light source is energized, and the usage condition obtaining system may include a timer, and a time measuring system which measures a total time period for which the light source is energized using the timer based on detection results output by the detecting system. In this case, the status data may include the detection result of the detecting system, and the usage condition may include the total time period.

Alternatively or optionally, the usage status monitoring system may include a detecting system which determines whether the endoscope processor is supplied with power, and the usage condition obtaining system may include a timer, and a time measuring system which measures a total time period for which the endoscope processor is supplied with power using the timer based on detection result output by the detecting system. In this case, the status data may include the detection result of the detecting system, and the usage condition may include the total time period.

Still optionally, the electronic endoscope system may include an image recording system which records an image captured by a solid-state imaging element provided in the electronic endoscope onto a medium, the usage status monitoring system may include a detecting system which determines whether the image recording system records the image onto the medium, and the usage condition obtaining system may include a counting system which counts the number of times by which the image recording system records the image onto the medium based on detection result output by the detecting system. In this case, the status data includes the detection result of the detecting system, and the usage condition includes the number of times by which the image recording system records the image onto the medium.

In some embodiments, the electronic endoscope may include an instrument-inserting channel into which an instrument is inserted, the usage status monitoring system may include a detecting system which determines whether the instrument is inserted into the instrument-inserting channel, and the usage condition obtaining system may include a counting system which counts the number of times by which the instrument is inserted into the instrument-inserting channel based on detection result output by the detecting system. In this case, the status data includes the detection result of the second detecting system; and the usage condition includes the number of times by which the instrument is inserted into the instrument-inserting channel.

In a particular case, the detecting system may include a mechanical switch provided in the electronic endoscope, and the detecting system may determine whether the instrument is inserted into the instrument-inserting channel based on a signal output by the mechanical switch. A member of the mechanical switch is pressed when the instrument is inserted into the instrument-inserting channel.

Alternatively, the detecting system may include a light-emitting device and a photodetector which are provided in the electronic endoscope, and the detecting system may determine whether the instrument is inserted into the instrument-inserting channel based on a signal output by the photodetector. The light-emitting device and the photodetector are placed so that a light beam emitted by the light-emitting device is blocked by the instrument when the instrument is inserted into the instrument-inserting channel.

Optionally, the detecting system may be configured to detect the type of the instrument inserted into the instrument-inserting channel, and the counting system may categorize the number of times by which the instrument is inserted into the instrument-inserting channel by the type of the instrument.

In a particular case, the detecting system may include a bar code reader provided in the electronic endoscope, and the bar code reader may read a bar code on the instrument when the instrument is inserted into the instrument-inserting channel. In this case, the bar code on the instrument represents the type of the instrument.

According to another aspect, there is provided a method for obtaining a usage condition of an electronic endoscope system, which includes monitoring a usage status of an electronic endoscope system and outputting status data, obtaining a usage condition of the electronic endoscope system based on the status data, and updating the usage condition based on the status data successively output.

BRIEF DESCRIPTION OF THE ACCOMPANYING DRAWINGS

FIG. 1 schematically shows an entire configuration of an electronic endoscope system according to an embodiment of the invention;

Figure 6A:
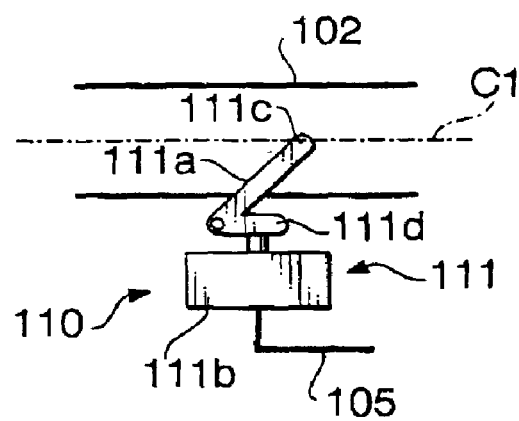
Figure 6B:
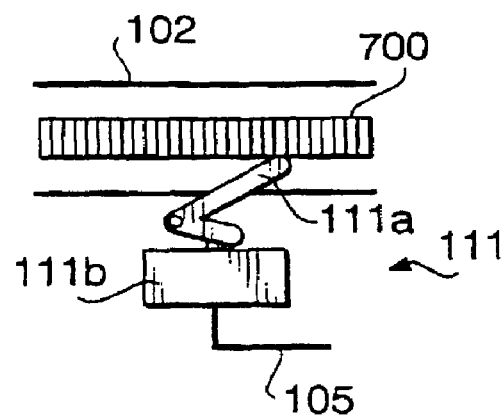

FIGS. 6A and 6B schematically show a instrument detecting unit having a microswitch.

Figure 7A:
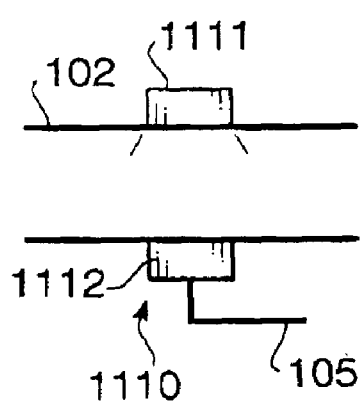
Figure 7B:
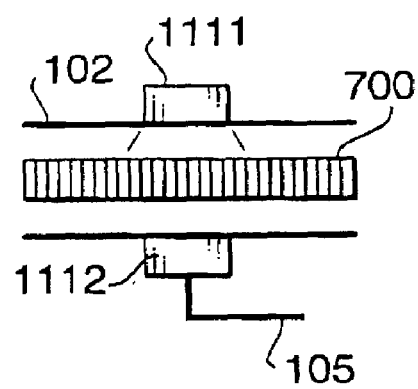
Figure 8:
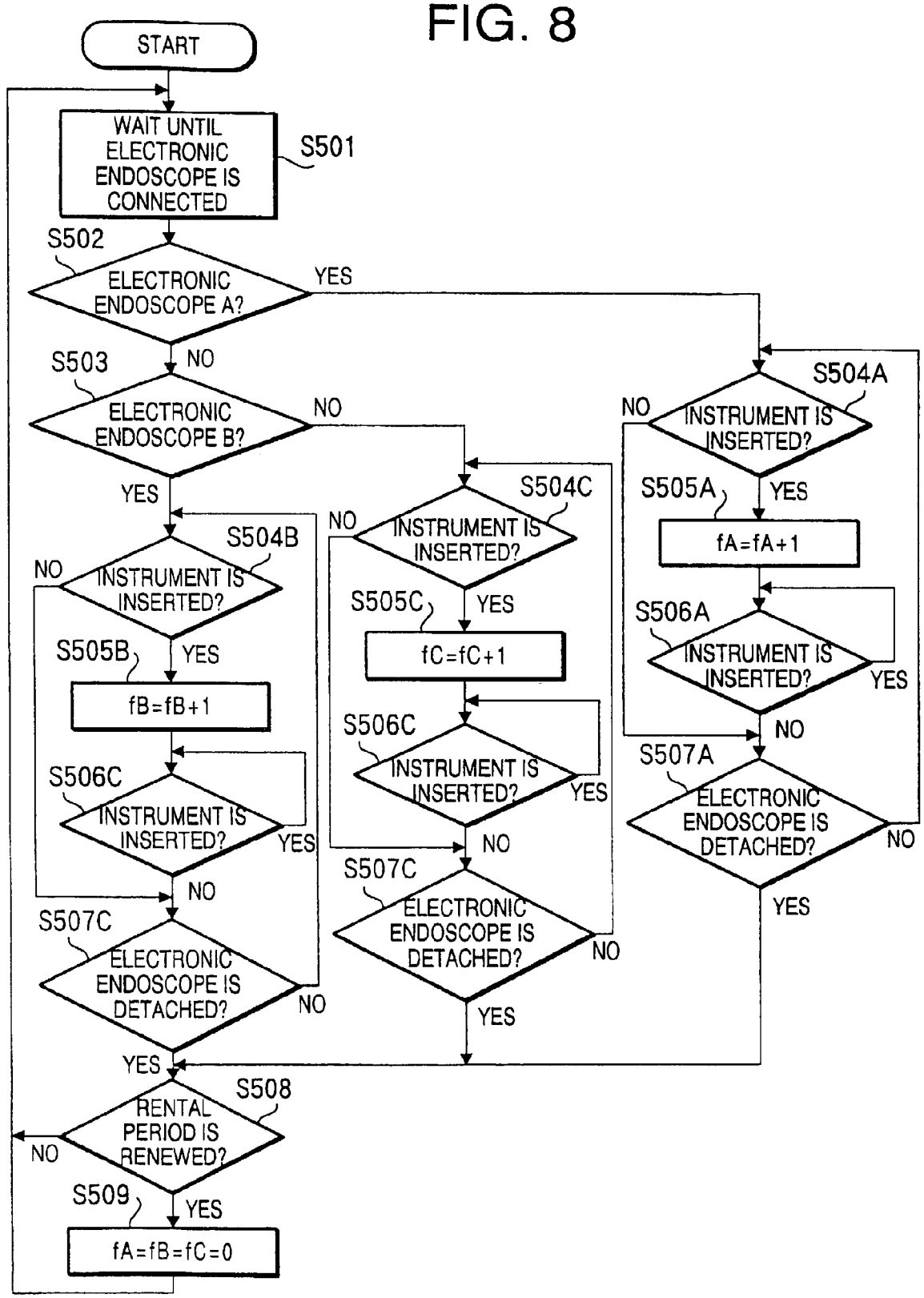
Figure 9A:
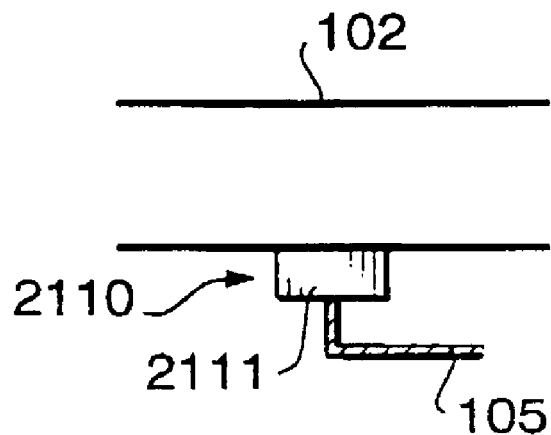
Figure 9B:
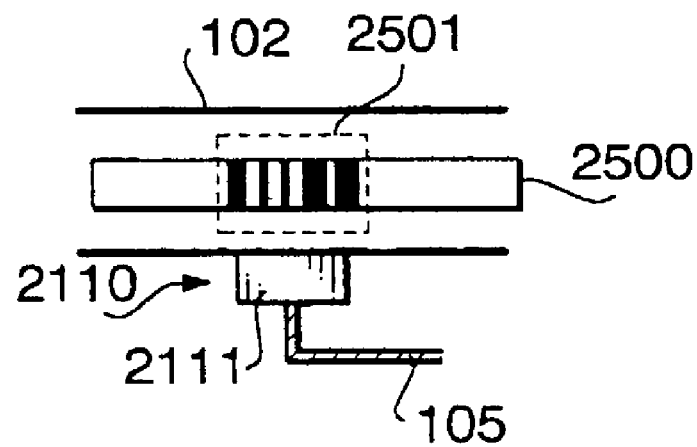
Figure 10:
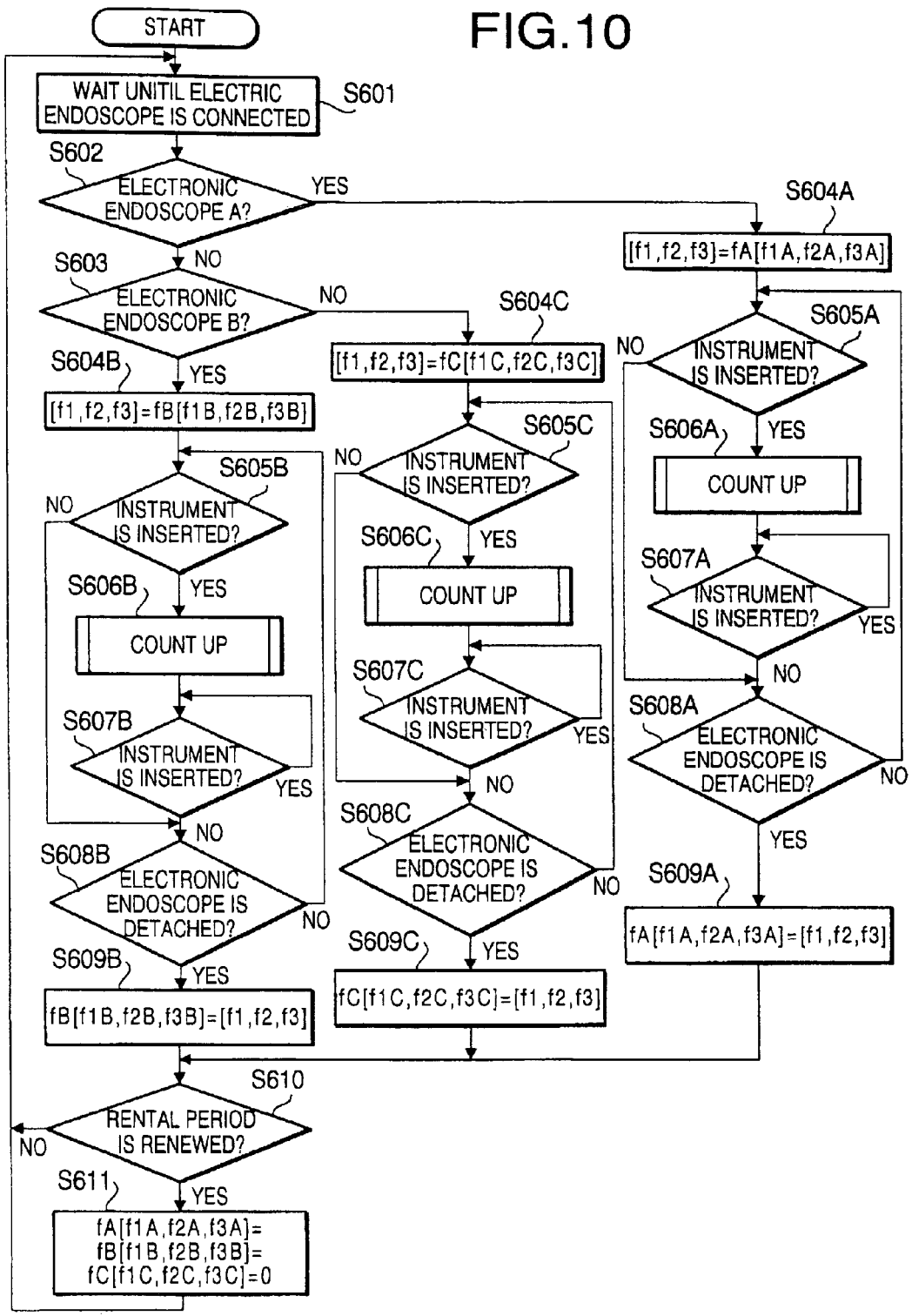
Figure 11:
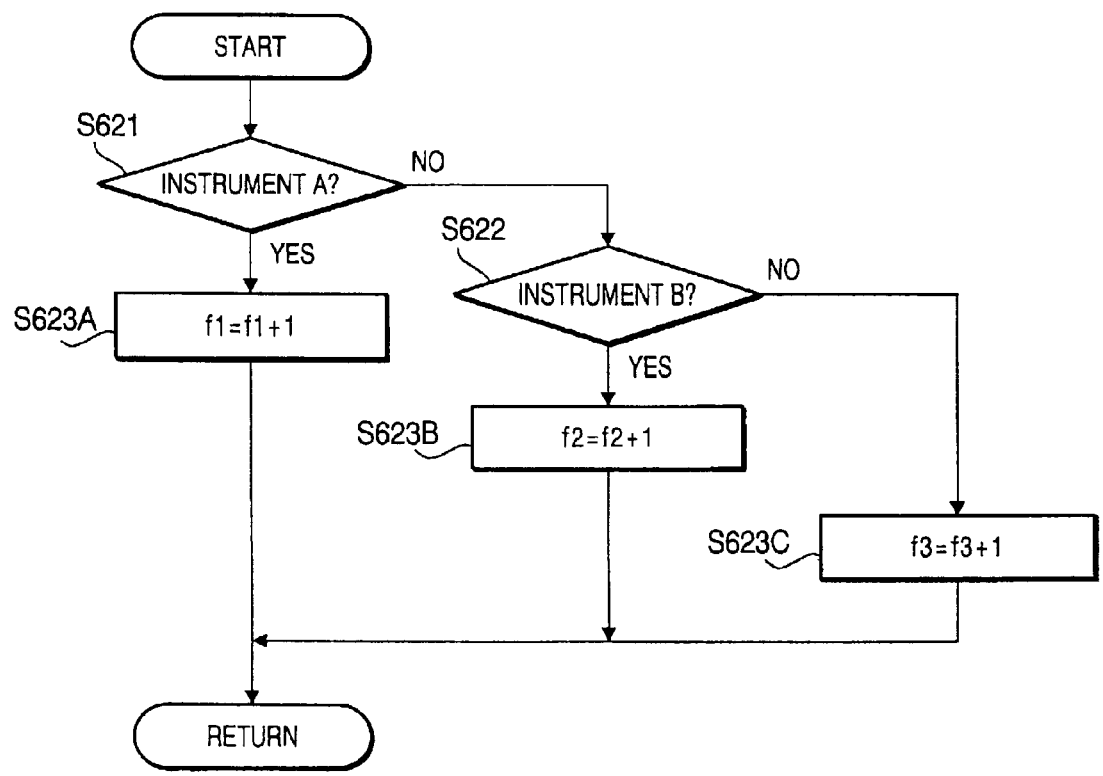

FIGS. 7A and 7B schematically show a instrument detecting unit having a light source and a photodetector;

FIG. 8 is a flowchart illustrating a procedure for calculating the number of times by which an instrument is inserted into an instrument-inserting channel, in which categorization by the type of the electronic endoscope is performed;

FIGS. 9A and 9B schematically show an instrument detecting unit having a bar code reader;

FIG. 10 is a flowchart illustrating a procedure for counting the total number of times that the instrument is inserted into the instrument-inserting channel, in which categorization in terms of the type of the electronic endoscope and the type of the instrument is performed;

FIG. 11 shows a subroutine called at S606A, S606B or S606C in FIG. 10; and

Figure 12:
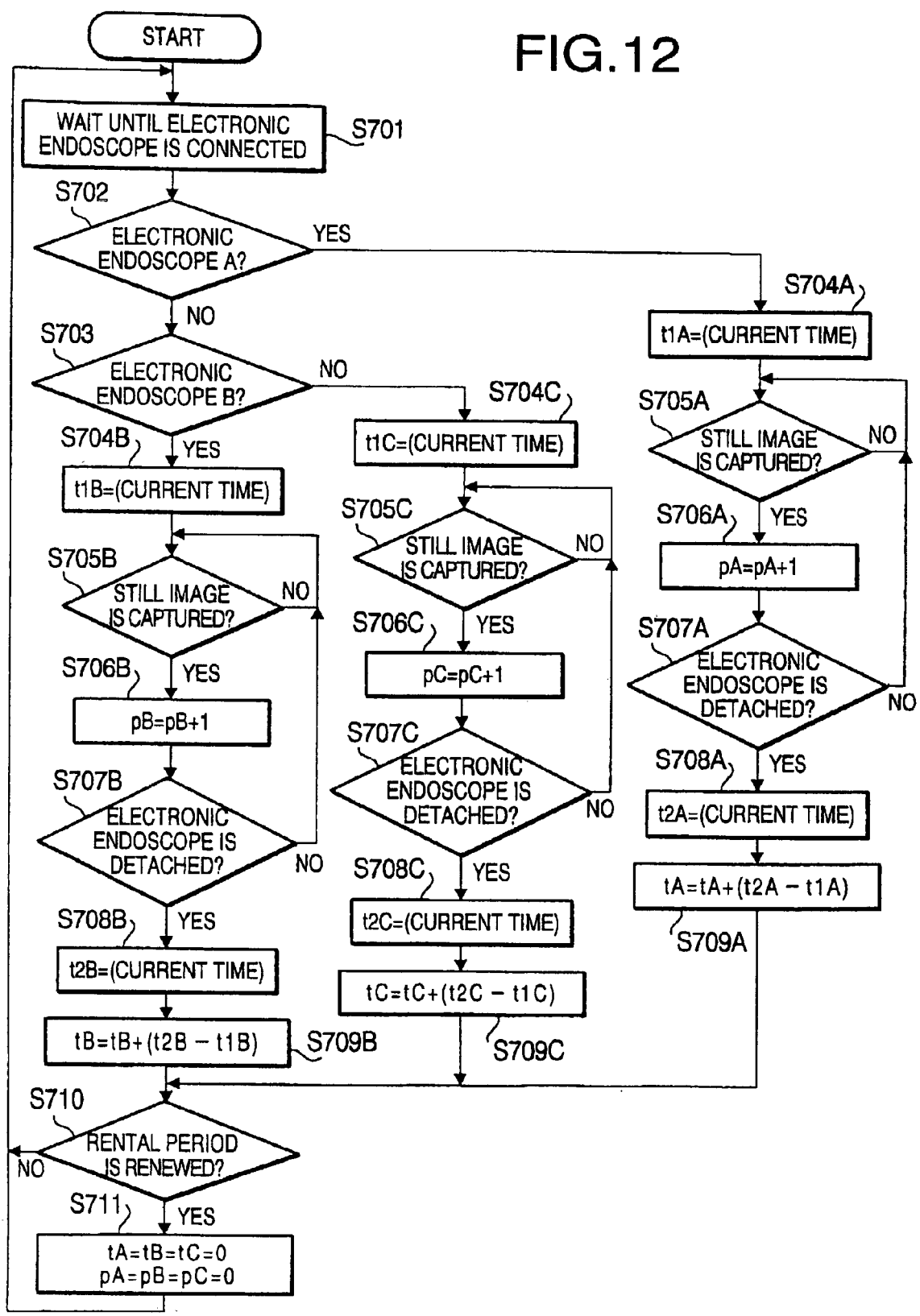

FIG. 12 is a flowchart illustrating a procedure for calculating a rental fee based on both of the time period of use of the electronic endoscope and the number of times that the still image is captured.

DETAILED DESCRIPTION OF THE EMBODIMENTS

Hereinafter, endoscope systems according to embodiments of the invention will be described with reference to the accompanying drawings.

First Embodiment

Figure 1:
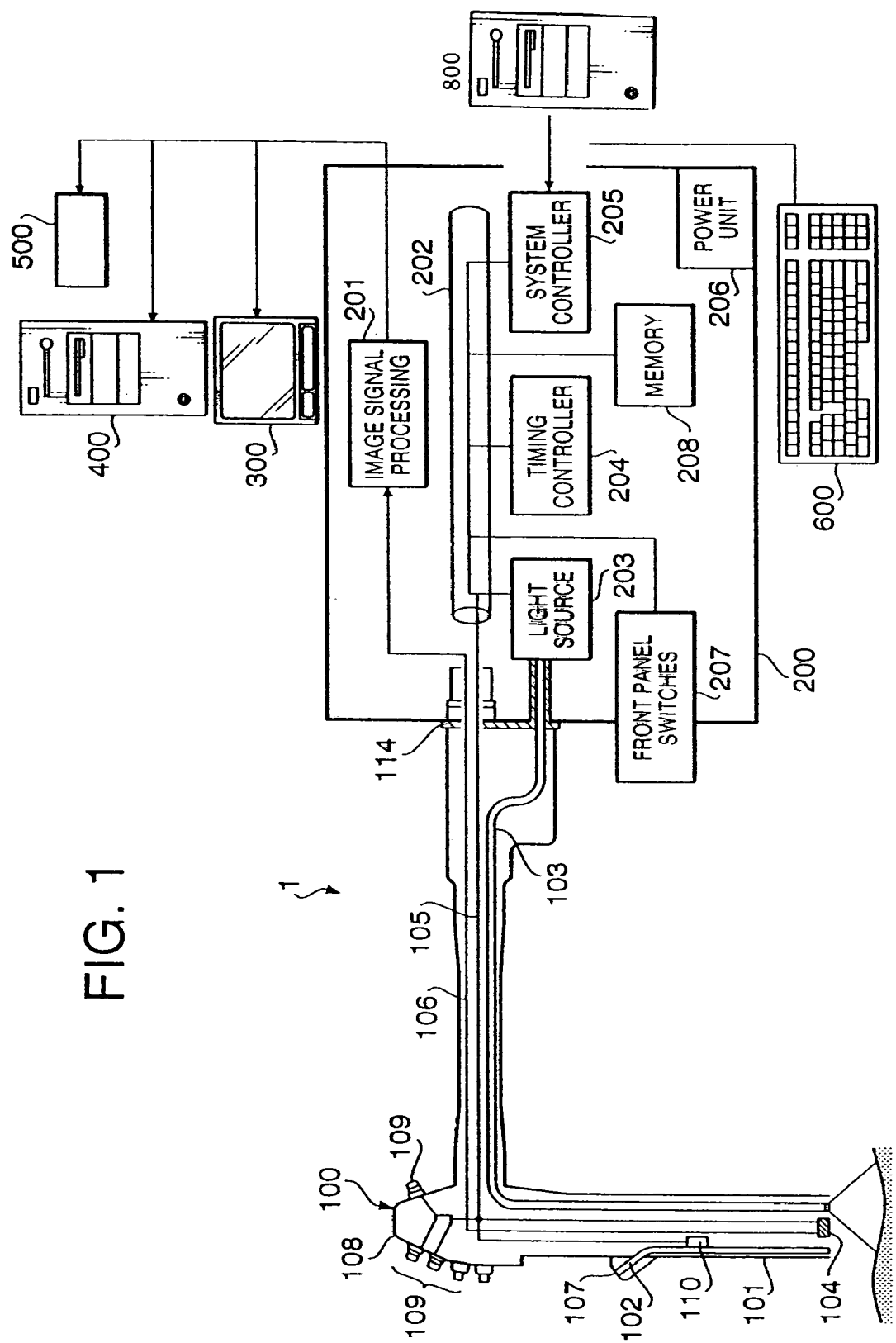

FIG. 1 schematically shows an entire configuration of an endoscope system 1 according to a first embodiment of the invention. The endoscope system 1 is provided with an electronic endoscope 100 and an endoscope processor 200 to which the electronic endoscope 100 is detachably attached.

The endoscope processor 200 is provided with a light source 203, a timing controller 204, a system controller 205, front panel switches 207, and a memory 208 that is a nonvolatile RAM, which are connected to each other via a bus 202. The endoscope processor 200 is further provided with an image signal processing circuit 201 and a power unit 206.

The timing controller 204 generates CCD drive signals for driving a CCD 104 provided at a tip portion of the electronic endoscope 100. The generated CCD drive signals are transmitted from the timing controller 204 to the CCD 104 through control signal cables 105 which are routed from a connecting portion 114 of the electronic endoscope 100 to the CCD 104.

The light source 203 emits light for illuminating an object to be observed to a light guide 103 provided in the electronic endoscope 100. The light emitted by the light source 203 reaches the tip portion of the electronic endoscope 100 propagating through the light guide 103 to illuminate an object.

The CCD 104 captures an optical image of the object and outputs an image signal which is transmitted to the image signal processing circuit 201 through an image signal cable 106 that is routed from the CCD 104 to the connecting portion 114 of the electronic endoscope 100. The image signal processing circuit 201 converts the image signal transmitted from the CCD 104 into a video signal such as an NTSC format video signal. The video signal is sent to a monitor 300, thereby images captured by the CCD 104 are displayed on the monitor 300. Additionally, the video signal may be sent to a computer 400 which functions as a medical image filing apparatus, a video printer 500, a VCR (not shown) or the like.

The system controller 205 controls all the circuits inside the endoscope processor 200. Further, the system controller 205 is connected with a keyboard 600, and controls the respective circuits based on input commands through the keyboard 600. Various functions including mode change, a superimposing of letters on the image, and image processing such as color balance adjustment, edge enhancement, or the like are performed under control of the system controller 205.

The electronic endoscope 100 and the endoscope processor 200 are configured such that the voltage level of an input signal to the system controller 205 varies depending on whether the electronic endoscope 100 is connected to the endoscope processor 200 or not, the system controller 205 can determine whether the electronic endoscope 100 is connected to the endoscope processor 200.

The system controller 205 is further connected with the front panel switches 207. The system controller 205 controls respective circuits based on input commands through the front panel switches 207. For example, by operating a switch of the front panel switches 207, a still image captured by the CCD 104 can be stored in an image memory (not shown) as a still image data. Further, by operating the front panel switches 207, the still image data stored in the image memory can be transmitted to the computer 400 and the video printer 500 which prints out the still image.

An instrument-insetting channel 102 is provided in the insertion tube 101 of the electronic endoscope 100. An instrument is inserted into the instrument-inserting, channel 102 via an instrument-opening 107 until it is exposed at the distal end of the insertion tube 101.

An operation unit 108 of the electronic endoscope 100 is provided with control switches 109. As in the case where the front panel switches 207 are used, the endoscope system 1 can be operated by operating the control switches 109. For example, by operating a certain switch of the control switches 109, a still image captured by the CCD 104 can be stored in the image memory (not shown) as a still image data. Further, by operating the other switch of the control switches 109, the still image data stored in the image memory can be transmitted to the computer 400 and the video printer 500 which prints out the still image.

Further, the system controller 205 is configured to monitor operation of the endoscope system 1 and obtains the following information:

(a) a type of the electronic endoscope 100 connected to the endoscope processor 200;
(b) a type of the instrument inserted into the instrument-inserting channel 102;
(c) a total number of times by which the electronic endoscope 100 is used (i.e., inserted into a body cavity);
(d) a total time period for which the electronic endoscope 100 is used (i.e., inserted into a body cavity);
(e) a total time period for which the endoscope processor 200 is supplied with power;
(f) a total time period for which a lamp in the light source 203 is energized;
(g) a total number of times by which the still image is captured (e.g., the total number of times by which the still image is printed out using the video printer 500);
(h) a total number of times by which the instrument is inserted into the instrument-inserting channel 102; and
(i) a total time period for which the instrument is inserted into the instrument-inserting channel 102. The above information (a)–(i) is stored in the memory 208 under the control of the system controller 205.

Preferably, the total number of times for which the electronic endoscope 100 is used and the total time period for which the electronic endoscope 100 is used are categorized by the type of the electronic endoscope (i.e., the kind of the electronic endoscope). The type of the electronic endoscope can be determined based on a manufacturing number of the electronic endoscope. The manufacturing number may be stored in a memory incorporated in the electronic endoscope 100 (not shown). When the electronic endoscope 100 is connected to the endoscope processor 200, the system controller 205 reads out the manufacturing number from the memory of the electronic endoscope 100, and determines the type of the connected electronic endoscope 100.

Alternatively, the total number of times for which the electronic endoscope 100 is used and the total time period for which the electronic endoscope 100 is used may be categorized by the manufacturing number of the electronic endoscope.

Preferably, the number of times by which the instrument is inserted into the instrument-inserting channel 102 and the total time period of insertion of the instrument are categorized by the type of the instrument (i.e., the kind of the instrument) or a manufacturing number of the instrument.

Figure 2:
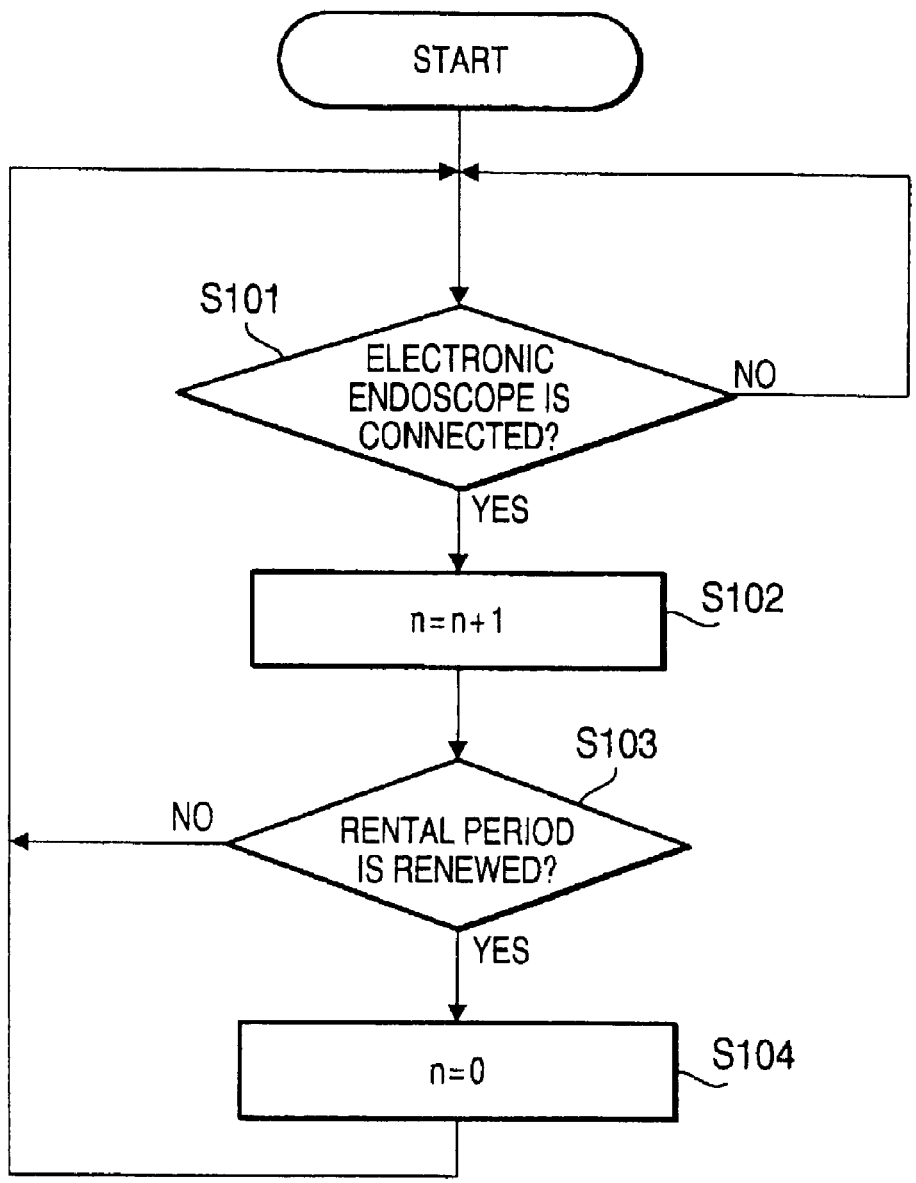
FIG. 2 is a flowchart illustrating a procedure for counting the number of times that an electronic endoscope is used, in which categorization in terms of the type of the electronic endoscope is not performed.

FIG. 2 is a flowchart illustrating a procedure for obtaining the number of times by which the electronic endoscope is used (i.e., inserted into a body cavity), according to the first embodiment of the invention. This procedure is performed under control of the system controller 205. It should be noted that FIG. 2 shows a case where categorization according to the type of the electronic endoscope connected to the endoscope processor is not performed. The number of times by which the electronic endoscope is used is represented by a variable "n" in FIG. 2.

The procedure shown in FIG. 2 starts when power of the endoscope processor 200 is turned on, and stays in a memory incorporated in the system controller 205 (not shown) while the endoscope processor 200 is supplied with power. Accordingly, the procedure shown in FIG. 2 is executed while the endoscope processor 200 is operated.

In S101, it is determined whether the electronic endoscope 100 is connected to the endoscope processor 200 or not. Step S101 is repeated until the electronic endoscope 100 is connected to the endoscope processor 200. If the electronic endoscope 100 is connected to the endoscope processor 200 (S101:YES), control proceeds to S102. In S102, the variable "n" is incremented by 1.

Next, it is determined whether the time period of a rental use contract of the endoscope system 1 is to be renewed or not based on directions input to the endoscope processor 200 by the service person via, for example, the keyboard 600 (S103). Alternatively, the directions may be transmitted from an external computer 800 which is connected to the endoscope processor 200 via an interface connector of the endoscope processor 200 (not shown).

If the time period of the rental use contract is not to be renewed (S103:NO), control returns to S101. If the time period of the rental use contract is renewed (S103:YES), "n" is reset to 0 (S104). Then, control returns to S101.

Thus, "n" represents the total number of times by which the electronic endoscope is used during the time period of the rental use contract. The service person obtains the value of "n" in S103 through, for example, the monitor 300. It should be noted that the variable "n" is stored in the memory 208 which is a nonvolatile RAM, and thus, is maintained even though the endoscope processor 200 is turned OFF.

Alternatively, the procedure shown in FIG. 2 may be executed by, for example, a microprocessor provided in the electronic endoscope 100 (not shown).

If the time period of the rental use contract is to be renewed (S103:YES), the rental fee (P1) is calculated according to the following equation:

$$P1 = n \times m1 \quad (1)$$

where m1 represents a charge for each use of the electronic endoscope. The service person charges the user the rental fee P1.

Second Embodiment

Figure 3:
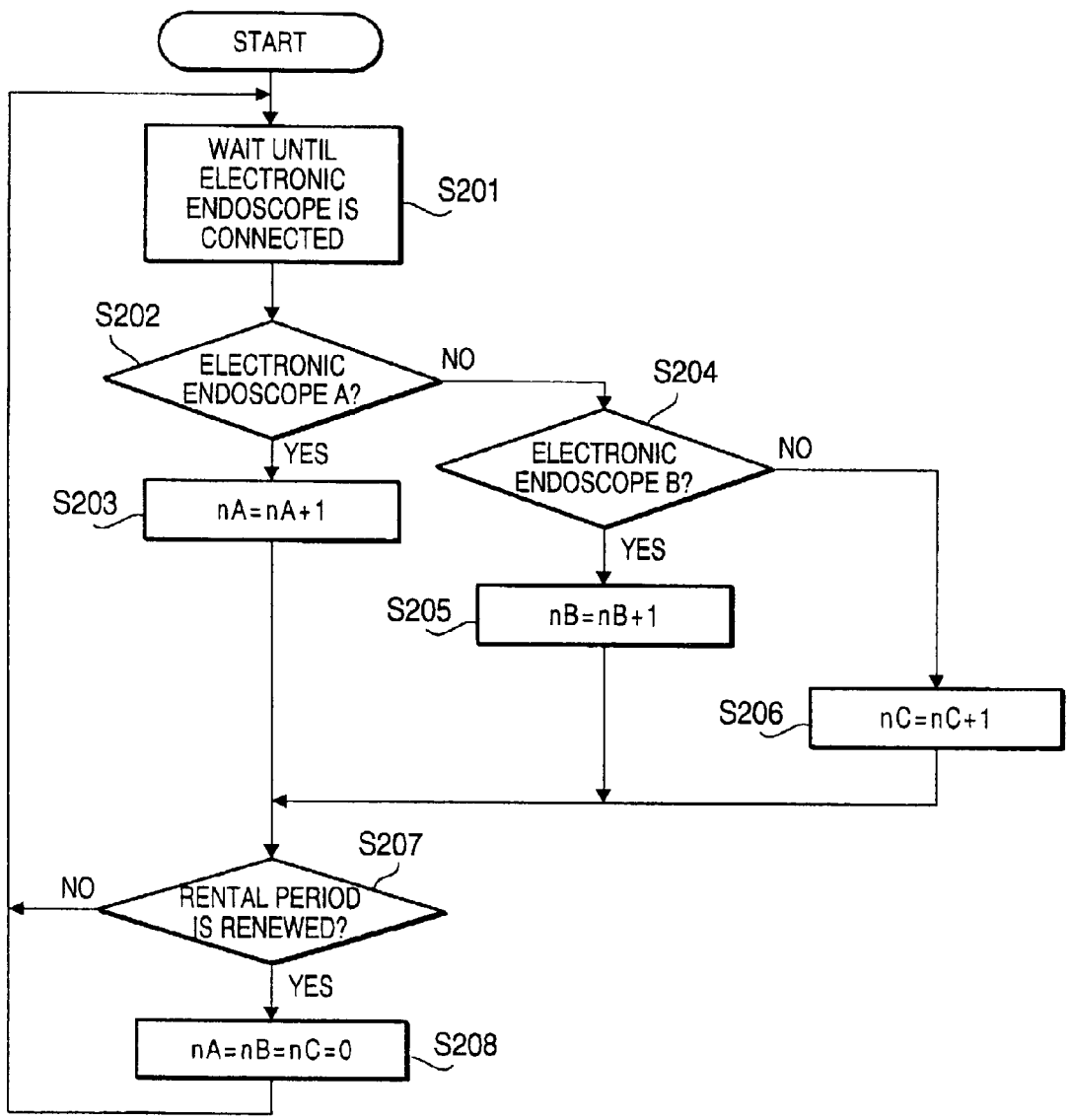
FIG. 3 is a flowchart illustrating a procedure for counting the number of times by which the electronic endoscope is used, in which categorization by the type of the electronic endoscope is performed.

FIG. 3 is a flowchart illustrating a procedure for obtaining the number of times by which the electronic endoscope is used, according to a second embodiment of the invention. This procedure includes categorizing the number of times by the type of the electronic endoscope connected to the endoscope processor 200. It should be noted that an entire configuration of an endoscope system according to the second embodiment is substantially the same as the endoscope system 1 (FIG. 1).

This procedure is performed under control of the system controller 205. Variables "nA", "nB" and "nC" in FIG. 3 represent the number of times of use of the electronic endoscopes of type-A, type-B and the other types, respectively.

The procedure shown in FIG. 3 starts when power of the endoscope processor 200 is turned on, and stays in the memory while the endoscope processor 200 is supplied with power. Accordingly, the procedure shown in FIG. 3 is executed while the endoscope processor 200 is operated. Variables "nA", "nB" and "nC" are stored in the memory 208, and therefore, variables "nA", "nB" and "nC" are maintained even though the endoscope processor 200 is turned OFF.

In S201, it is determined whether the electronic endoscope 100 is connected to the endoscope processor 200. Step S201 is repeated until the electronic endoscope 100 is connected to the endoscope processor 200. If the electronic endoscope 100 is connected to the endoscope processor 200, control proceeds to S202.

In S202, it is determined whether the electronic endoscope 100 connected to the endoscope processor 200 is type-A or not. If the electronic endoscope 100 connected to the endoscope processor 200 is type-A (S202:YES), control proceeds to S203. In S203, the variable "nA" is incremented by 1. Then, control proceeds to S207.

If the electronic endoscope 100 connected to the endoscope processor 200 is not type-A (S202:NO), control proceeds to S204 where it is determined whether the electronic endoscope 100 connected to the endoscope processor 200 is type-B or not. If the electronic endoscope 100 connected to the endoscope processor 200 is type-B (S204:YES), control proceeds to S205. In S205, the variable "nB" is incremented by 1. Then, control proceeds to S207.

If the electronic endoscope 100 connected to the endoscope processor 200 is not type-B (S204:NO), control proceeds to S206 where the variable "nC" is incremented by 1. Then, control proceeds to S207.

Next, it is determined whether the time period of a rental use contract is to be renewed or not based on directions input to endoscope processor 200 by the service person via, for example, the keyboard 600 (S207).

If the time period of the rental use contract is not to be renewed (S207:NO), control returns to S201. If the time period of the rental use contract is to be renewed (S207:YES), variables "nA", "nB" and "nC" are reset to 0 (S208). Then, control returns to S201.

Thus, variables "nA", "nB" and "nC" represent the total number of times of use of the electronic endoscope of type-A, type-B and the other types, respectively, during the time period of the rental use contract. The service person obtains values of "nA", "nB" and "nC" in S207 through, for example, the monitor 300.

If the time period of the rental use contract is to be renewed (S207:YES), the rental fee (P2) is calculated according to the following equation:

$$P2 = nA \times m1A + nB \times m1B + nC \times m1C \quad (2)$$

where a coefficient m1A represents a charge for each use of the electronic endoscope of type-A, a coefficient m1B represents a charge for each use of the electronic endoscope of type-B and a coefficient m1C represents a charge for each use of the other types of the electronic endoscopes. The service person charges the user the rental fee P2.

As described above, the procedure shown in FIG. 3 enables collection of a rental fee that is related to the price of the electronic endoscope connected to the endoscope processor. It should be noted that the kinds of endoscopes connectable to the endoscope processor 200 is not limited to three, but the endoscope system may be configured such that two or more than three types of electronic endoscopes and/or two or more electronic endoscopes of the same type could be connected to the endoscope processor 200, and the fee is calculated in a similar manner. For example, the number of times by which the electronic endoscopes is used may be categorized into, four groups using four variables "nA", "nB", "nC" and "nD" in a similar manner.

Third Embodiment

Figure 4:
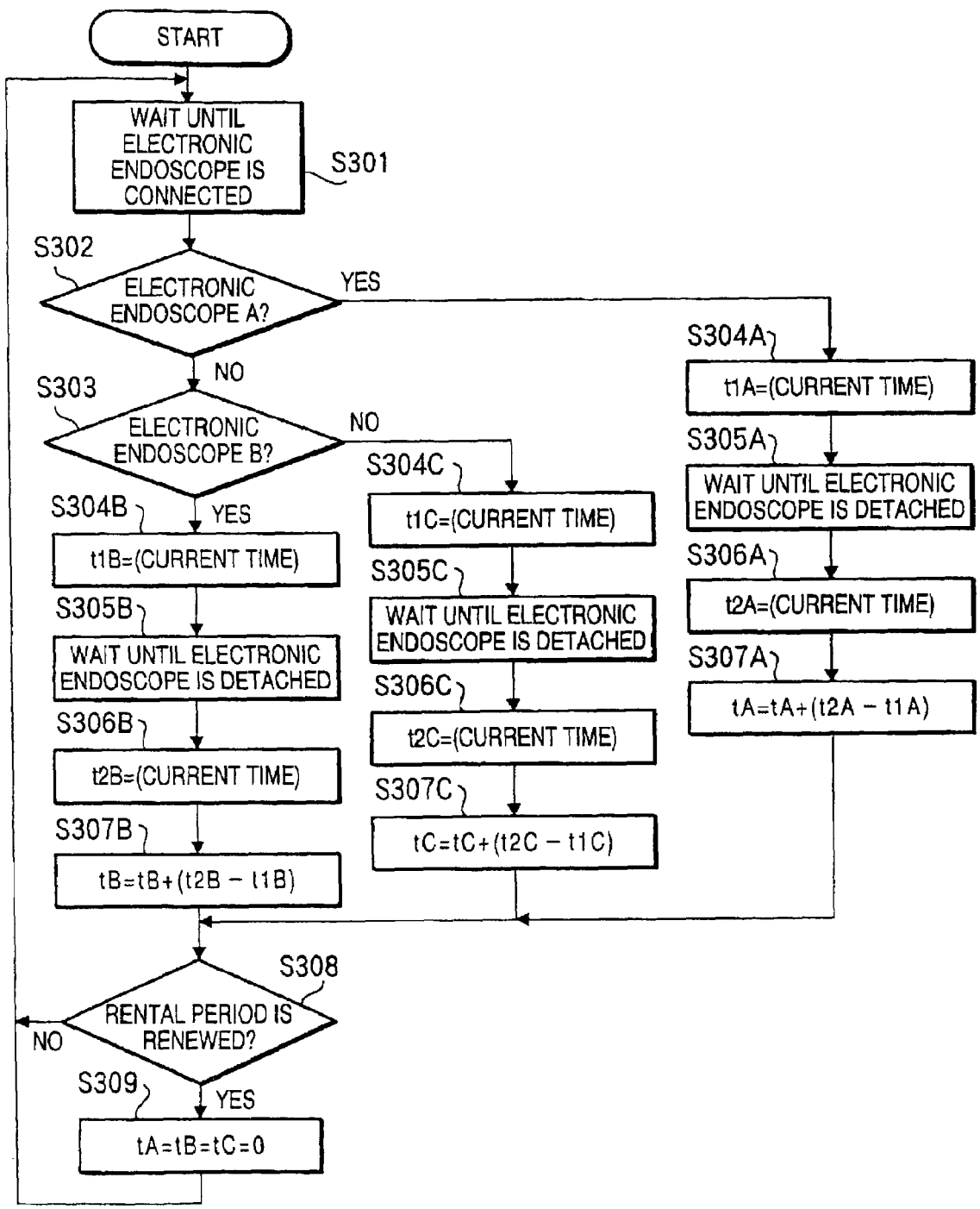
FIG. 4 is a flowchart illustrating a procedure for measuring a time period for which the electronic endoscope is used, in which categorization by the type of the electronic endoscope is performed.

FIG. 4 is a flowchart illustrating a procedure for obtaining the time period for which the electronic endoscope 100 is used (i.e., inserted into a body cavity), according to a third embodiment of the invention. This procedure includes categorizing the time period by the type of the electronic endoscope connected to the endoscope processor 200. It should be noted that an entire configuration of an endoscope system according to the third embodiment is substantially the same as the endoscope system 1 (FIG. 1).

This procedure (FIG. 4) is performed under control of the system controller 205. Variables "tA", "tB" and "tC" in FIG. 4 represent the time period of use of the electronic endoscopes of type-A, type-B and the other types, respectively.

The procedure shown in FIG. 4 starts when power of the endoscope processor 200 is turned on, and stays in the memory while the endoscope processor 200 is supplied with power. Accordingly, the procedure shown in FIG. 4 is executed while the endoscope processor 200 is operated. Variables "tA", "tB" and "tC" are stored in the memory 208, and therefore, variables "tA", "tB" and "tC" are maintained even though the endoscope processor 200 is turned OFF.

In S301, it is determined whether the electronic endoscope 100 is connected to the endoscope processor 200 or not. Step S301 is repeated until the electronic endoscope 100 is connected to the endoscope processor 200. If the electronic endoscope 100 is connected to the endoscope processor 200, control proceeds to S302.

In S302, it is determined whether the electronic endoscope 100 connected to the endoscope processor 200 is type-A or not. If the electronic endoscope 100 connected to the endoscope processor 200 is type-A (S302:YES), control proceeds to S304A.

In S304A, the time information when the electronic endoscope is connected to the endoscope processor 200 is assigned to a variable "t1A". Next, the system controller 205 waits until the electronic endoscope 100 is detached from the endoscope processor 200 (S305A).

If the electronic endoscope 100 is detached from the endoscope processor 200, control proceeds to S306A and the time information when the electronic endoscope 100 is detached from the endoscope processor 200 is assigned to a variable "t2A". In step S307A, the time period of use of the electronic endoscope of type-A (tA) is updated according to tA=tA+(t2A−t1A). Thus, the variable "tA" represents the total time period of use of the electronic endoscope of type-A. Next, control proceeds to S308.

If the electronic endoscope 100 connected to the endoscope processor 200 is not type-A (S302:NO), control proceeds to S303 where it is determined whether the electronic endoscope 100 connected to the endoscope processor 200 is type-B or not. If the electronic endoscope 100 connected to the endoscope processor 200 is type-B (S303:YES), control proceeds to S304B.

As in the case of the electronic endoscope of type-A (the steps of S304A–S307A), the time period of use of the electronic endoscopes of type-B (tB) is updated according to tB=tB+(t2B−t1B), through the steps of S304B–S307B, where the variable "t1B" represents the time information when the electronic endoscope of type-B is connected to the endoscope processor 200, and the variable "t2B" represents the time information when the electronic endoscope of type-B is detached from the endoscope processor 200. Thus, the variable "tB" represents the total time period of use of the electronic endoscope 100 of type-B. Next, control proceeds to S308.

If the electronic endoscope 100 connected to the endoscope processor 200 is not type-B (S303:NO), control proceeds to S304C. As in the case of the electronic endoscope of type-A (the steps of S304A–S307A), the time period of use of the other types of electronic endoscopes is updated according to tC=tC+(t2C−t1C), through the steps of S304C–S307C, where the variable "t1C" represents the time information when the other types of the electronic endoscope is connected to the endoscope processor 200, and the variable "t2C" represents the time information when the other types of the electronic endoscope is detached from the endoscope processor 200. Thus, the variable "tC" represents the total time period of use of the other types of the electronic endoscope. Next, control proceeds to S308.

In S308, it is determined whether the time period of a rental use contract is to be renewed or not based on directions input to endoscope processor 200 by the service person via, for example, the keyboard 600.

If the time period of the rental use contract is not to be renewed (S308:NO), control returns to S301. If the time period of the rental use contract is to be renewed (S308:YES), variables "tA", "tB" and "tC" are reset to 0 (S309). Then, control returns to S301.

Thus, variables "tA", "tB" and "tC" represent the total time period of use of the electronic endoscope of type-A, type-B; and the other types, respectively, during the time period of the rental use contract. The service person obtains values of "tA", "tB" and "tC" in S308 through, for example, the monitor 300.

If the time period of the rental use contract is to be renewed (S308:YES), the rental fee (P3) is calculated according to the following equation:

$$P3 = tA \times m2A + tB \times m2B + tC \times m2C \qquad (3)$$

where a coefficient m2A represents a charge per unit time regarding use of the electronic endoscope of type-A, a coefficient m2B represents a charge per unit time regarding use of the electronic endoscope of type-B, and a coefficient m2C represents a charge per unit time regarding use of the other types of the electronic endoscope. The service person charges the user the rental fee P3.

As described above, the procedure shown in FIG. 4 enables collection of rental fees which correspond to time of use of the respective electronic endoscopes.

It is also possible to calculate a rental fee (P3') without categorization of the time period of use of the electronic endoscope by the type of the electronic endoscope. The rental fee (P3') can be calculated according to the following equation:

$$P3' = (tA + tB + tC) \times m2 \qquad (4)$$

where a coefficient m2 represents a charge per unit time regarding use of the electronic endoscope, and m2 is common to every kind of the electronic endoscope.

Similarly, calculation of a rental fee according to the total time period for which the processor 200 is supplied with power with(or without) categorization by the type of the electronic endoscope can also be carried out. Also, calculation of a rental fee according to the total time period for which the lamp in the light source 203 is energized can be carried out.

Fourth Embodiment

Figure 5:
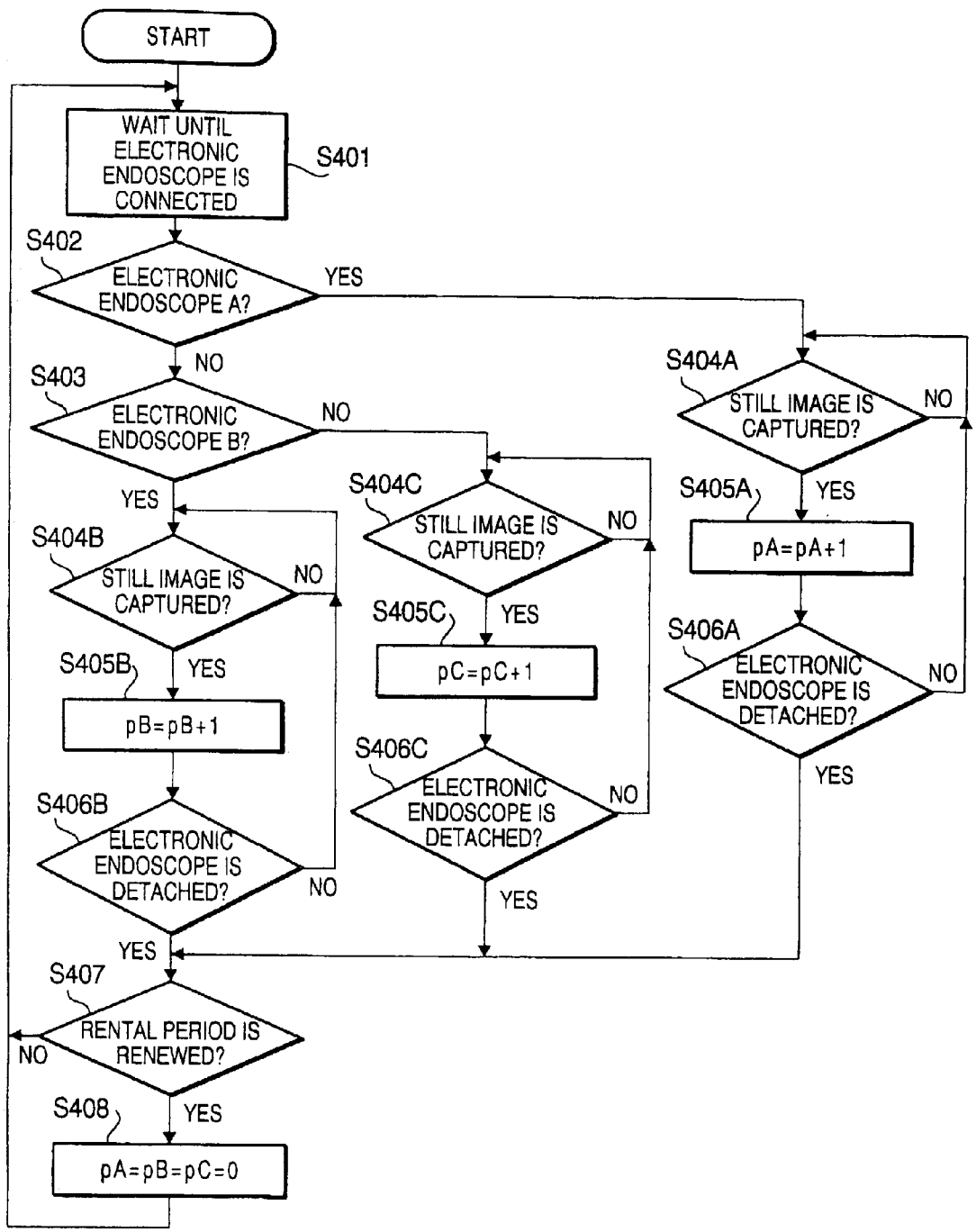
FIG. 5 is a flowchart illustrating a procedure for calculating the total number of times by which a still image is captured, in which categorization by the type of the electronic endoscope is performed.

FIG. 5 is a flowchart illustrating a procedure for obtaining the total number of times by which a still image is captured and printed out using the video printer 500, according to a fourth embodiment of the present invention. This procedure includes categorizing the total number of times by the type of the electronic endoscope connected to the endoscope processor 200. It should be noted that an entire configuration of an endoscope system according to the forth embodiment is substantially the same as the endoscope system 1 (FIG. 1).

As described above, the user operates a certain switch (a capturing switch) of the control switches 109 to capture (or to print out) the still image. When the capturing switch is operated, a signal which indicates operation of the capturing switche is transmitted to the system controller 205. The system controller 205 counts the number of times by which the signal indicating operation of the capturing switch is input to it. Accordingly, the system controller 205 can obtain the number of times by which the still image is captured (printed).

This procedure is performed under control of the system controller 205. A variable "pA" in FIG. 5 represents the number of times by which the still image is captured when the electronic endoscopes of type-A is used. A variable "pB" in FIG. 5 represents the number of times by which the still image is captured when the electronic endoscopes of type-B is used. A variable "pC" in FIG. 5 represents the number of times by which the still image is captured when the other types of the electronic endoscope is used.

The procedure shown in FIG. 5 starts when power of the endoscope processor 200 is turned on, and stays in the memory while the endoscope processor 200 is supplied with power. Accordingly, the procedure shown in FIG. 5 is executed while the endoscope processor 200 is operated. Variables "pA", "pB" and "pC" in FIG. 5 are stored in the memory 208, and therefore, variables "pA", "pB" and "tC" are maintained even though the endoscope processor 200 is turned OFF.

In S401, it is determined whether the electronic endoscope 100 is connected to the endoscope processor 200 or not. Step S401 is repeated until the electronic endoscope 100 is connected to the endoscope processor 200. If the electronic endoscope 100 is connected to the endoscope processor 200, control proceeds to S402.

In S402, it is determined whether the electronic endoscope 100 connected to the endoscope processor 200 is type-A or not. If the electronic endoscope 100 connected to the endoscope processor 200 is type-A (S402:YES), control proceeds to S404A.

In S404A, the system controller 205 waits until the signal indicating capture operation of the control switches 109 is input to it. If the signal indicating capture operation of the control switches 109 is input (S404A:YES), i.e., the still image is captured, the variable "pA" is incremented by 1 (S405A).

Next, it is determined whether the electronic endoscope 100 is detached from the endoscope processor 200 (S406A). If the electronic endoscope 100 is not detached (S406A: NO), control returns to S404A. If the electronic endoscope 100 is detached (S406A:YES), control proceeds to S407.

If the electronic endoscope 100 connected to the endoscope processor 200 is not type-A (S402:NO), control proceeds to S403 where it is determined whether the electronic endoscope 100 connected to the endoscope processor 200 is type-B or not. If the electronic endoscope 100 connected to the endoscope processor 200 is type-B (S403:YES), control proceeds to S404B.

As in the case of the electronic endoscope of type-A (the steps of S404A–S406A,), the number of times by which the still image is captured using the electronic endoscope of type-B (pB) is updated according to pB=pB+1 (the steps of S404B–S406B). Next, control proceeds to S407.

If the electronic endoscope 100 connected to the endoscope processor 200 is not type-B (S403:NO), control proceeds to S404C. As in the case of the electronic endoscope of type-A (the steps of S404A–S406A), the number of times by which the still image is captured using the other types of the electronic endoscope is updated according to pC=pC+1 (the steps of S404C–S406C). Next, control proceeds to S407.

In S407, it is determined whether the time period of a rental use contract is to be renewed or not based on directions input to the endoscope processor 200 by the service person via, for example, the keyboard 600. If the time period of the rental use contract is not to be renewed (S407:NO), control returns to S401. If the time period of the rental use contract is to be renewed (S407:YES), variables "pA", "pB" and "pC" are reset to 0 (S408). Next, control returns to S401.

Thus, variables "pA", "pB" and "pC" represent the total number of times by which the still image is captured using the electronic endoscope of type-A, type-B and the other types, respectively, during the time period of the rental use contract. The service person obtains values of "pA", "pB" and "pC" in S407 through, for example, the monitor 300.

If the time period of the rental use contract is to be renewed (S407:YES), the rental fee (P4) is calculated according to the following equation:

$$P4 = pA \times m3A + pB \times m3B + pC \times m3C \qquad (5)$$

where the coefficient m3A represents a charge for each capture of a still image regarding use of the electronic endoscope of type-A, the coefficient m3B represents a charge for each capture of a still image regarding use of the electronic endoscope of type-B, and the coefficient m3C represents a charge for each capture of a still image regarding the use of the other types of electronic endoscope. The service person charges the user the rental fee P4.

It is also possible to calculate a rental fee (P4') without categorization of the number of times by which the still image is captured based on the type of the electronic endoscope. The rental fee (P4') can be calculated according to the following equation:

$$P4' = (pA + pB + pC) \times m3 \qquad (6)$$

where the coefficient m3 represents a charge for each capture of a still image, and m3 is common to every kind of the electronic endoscope.

Fifth Embodiment

A fifth embodiment of the invention will be described below with reference to FIGS. 6A–6B, FIGS. 7A–7B and FIG. 8. It should be noted that an entire configuration of an endoscope system according to the fifth embodiment is substantially the same as the endoscope system 1 (FIG. 1).

An instrument detecting unit 110 which detects the instrument when the instrument is inserted into the instrument-inserting channel 102 is provided in the electronic endoscope 100 (FIG. 1). Further, the instrument detecting unit 110 is connected to the system controller 205 through the control signal cables 105. The system controller 205 counts the number of-times by which the instrument is inserted into the instrument-inserting channel 102 based on the signal output by the instrument detecting unit 110.

FIG. 6A schematically shows the instrument detecting unit 110. The instrument detecting unit 110 has a microswitch 111 which is provided with a lever 111a and a switch case 111b. FIG. 6A shows a case where the instrument 700 is not inserted into the instrument-inserting channel 102. The lever 111a is pressed by a spring (not shown) such that a-tip portion 111c thereof is located at a center line C1 of the instrument-inserting channel 102.

FIG. 6B shows a case where the instrument 700 is inserted into the instrument-inserting channel 102. As shown in FIG. 6B, the lever 111a is pressed down by the instrument 700, and therefore, the lever 111a is in the "down" position.

When the lever 111a is pressed by the instrument 700 and it is in the "down" position, another tip portion 111d of the lever 111a presses the switch case 111b. When the switch case 111b is pressed by the lever 111a, a signal indicating insertion of the instrument 700 is transmitted from the microswitch 111 to the system controller 205 through the control signal cables 105. Therefore, the system controller 205 can determine whether the instrument 700 is inserted into the instrument-inserting channel 102 or not.

With this configuration, the system controller 205 can count the number of times by which the instrument is inserted into the instrument-inserting channel 102.

As an alternative to the instrument detecting unit 110 shown in FIG. 6A, FIG. 7A schematically shows a instrument detecting unit 1110 which has a light source 1111 such as a LED (Light-Emitting Diode) and a photodetector 1112. FIG. 7A shows a case where the instrument 700 is not inserted into the instrument-inserting channel 102. In this case, light emitted by the light source 1111 impinges on the photodetector 1112, and therefore, a signal which indicates the instrument 700 is not inserted into the instrument-inserting channel 102 is transmitted from the photodetector 1112 to the system controller 205 through the control signal cables 105.

FIG. 7B shows a case where the instrument 700 is inserted into the instrument-inserting channel 102. As shown in FIG. 7B, light emitted by the light source 1111 does not impinge on the photodetector 1112. In this case, a signal indicating insertion of the instrument 700 is transmitted to the system controller 205 through the control signal cables 105.

Therefore, the-system controller 205 can determine whether the instrument 700 is inserted into the instrument-inserting channel 102 or not. With this configuration, the system controller 205 can count the number of times by which the instrument is inserted into the instrument-inserting channel 102.

FIG. 8 is a flowchart illustrating a procedure for obtaining the number of times by which the instrument is inserted into the instrument-inserting channel 102, according to the fifth embodiment of the invention. This procedure includes categorization by the type of the electronic endoscope. This procedure is performed under control of the system controller 205.

A variable "fA" in FIG. 8 represents the number of times by which the instrument is inserted into the instrument-inserting channel 102 when the electronic endoscopes of type-A is used. A variable "fB" in FIG. 8 represents the number of times by which the instrument is inserted into the instrument-inserting channel 102 when the electronic endoscopes of type-B is used. A variable "fC" represents the number of times by which the instrument is inserted into the instrument-inserting channel 102 when the other types of electronic endoscope is used.

The procedure shown in FIG. 8 starts when power of the endoscope processor 200 is turned on, and stays in the memory while the endoscope processor 200 is supplied with power. Accordingly, the procedure shown in FIG. 8 is executed while the endoscope processor 200 is operated. Variables "fA", "fB", and "fC" are stored in the memory 208, and therefore, variables "fA", "fB" and "fC" are maintained even though the endoscope processor 200 is turned OFF.

In S501, it is determined whether the electronic endoscope 100 is connected to the endoscope processor 200 or not. Step S501 is repeated until the electronic endoscope 100 is connected to the endoscope processor 200. If the electronic endoscope 100 is connected to the endoscope processor 200, control proceeds to S502.

In S502, it is determined whether the electronic endoscope 100 connected to the endoscope processor 200 is type-A or not. If the electronic endoscope 100 connected to the endoscope processor 200 is type-A (S502:YES), control proceeds to S504A.

In S504A, it is determined whether the signal indicating insertion of the instrument is input to the system controller 205 or not. If the signal indicating insertion of the instrument is input (S504A:YES), i.e., the instrument is inserted into the instrument-inserting channel 102, the variable "fA" is incremented by 1 (S505A). If the signal indicating insertion of the instrument is not input (S504A:NO), control proceeds to S507A.

In S506A, it is determined whether the signal indicating insertion of the instrument is input to the system controller 205 or not. If the instrument is inserted into the instrument-inserting channel 102 (S506A:YES), i.e., the instrument is staying in the instrument-inserting channel 102, S506A is repeated. If the signal indicating insertion of the instrument is not input (S506A:NO), i.e., the instrument is pulled out of the instrument-inserting channel 102 (S506A:NO), control proceeds to S507A.

In S507A, it is determined whether the electronic endoscope 100 is detached from the endoscope processor 200 or not. If the electronic endoscope 100 is not detached (S507A:NO), control returns to S504A. If the electronic endoscope 100 is detached (S507A:YES), control proceeds to S508.

If the electronic endoscope 100 connected to the endoscope processor 200 is not type-A (S502:NO), control proceeds to S503 where it is determined whether the electronic endoscope 100 connected to the endoscope processor 200 is type-B or not. If the electronic endoscope 100 connected to the endoscope processor 200 is type-B (S503:YES), control proceeds to S504B.

As in the case of the electronic endoscope of type-A (the steps of S504A–S507A), the number of times by which the instrument is inserted into the instrument-inserting channel 102 of electronic endoscopes of type-B (fB) is updated according to fB=fB+1 (the steps of S504B–S507B). Next, control proceeds to S508.

If the electronic endoscope 100 connected to the endoscope processor 200 is not type-B (S503:NO), control proceeds to S504C. As in the case of the electronic endoscope of type-A (the steps of S504A–S507A), the number of times by which the instrument is inserted into the instrument-inserting channel 102 of the other types of the electronic endoscopes (fC) is updated according to fC=fC+1 (the steps of S504C–S507C). Next, control proceeds to S508.

In S508, it is determined whether the time period of a rental use contract is to be renewed or not based on directions input to the endoscope processor 200 by the service person via, for example, the keyboard 600. If the time period of the rental use contract is not to be renewed (S508:NO), control returns to S501. If the time period of the rental use contract is renewed (S508:YES), variables "fA", "fB" and "fC" are reset to 0 (S509). Next, control returns to S501.

Thus, variables "fA", "fB" and "fC" represent the total number of times by which the instrument is inserted into the instrument-inserting channel 102 of the electronic endoscope of type-A, type-B and the other types, respectively, during the time period of the rental use contract. The service person obtains values of "fA", "fB" and "fC" in S508 through, for example, the monitor 300.

If the time period of the rental use contract is to be renewed (S508:YES), the rental fee (P5) is calculated according to the following equation:

$$P5 = fA \times m4A + fB \times m4B + fC \times m4C \qquad (7)$$

where the coefficient m4A represents a charge of use for each insertion of the instrument into the instrument-inserting channel 102 of the electronic endoscope of type-A, the coefficient m4B represents a charge of use for each insertion of the instrument into the instrument-inserting channel 102 of the electronic endoscope of, type-B, and the coefficient m4C represents a charge of use for each insertion of the instrument into the instrument-inserting channel 102 of the other types of the electronic endoscope. The service person charges the user the rental fee P5.

It is also possible to calculate a rental fee (P5') without categorization by the type of the electronic endoscope. In this case, the rental fee (P5') can be calculated according to the following equation:

$$P5' = (fA + fB + fC) \times m4 \qquad (8)$$

where a coefficient m4 represents a charge of use for each insertion of the instrument into the instrument-inserting channel 102, and m4 is common to every kind of the electronic endoscope.

Sixth Embodiment

A sixth embodiment of the invention will be described below with reference to FIGS. 9A–9B and FIG. 10. It should be noted that an entire configuration of an endoscope system according to the sixth embodiment is substantially the same as the endoscope system 1 (FIG. 1).

As an alternative to the instrument detecting unit 110 (FIG. 6A) or 1110 (FIG. 7A), FIG. 9A schematically illustrates a instrument detecting unit 2110 which has a bar code reader 2111 for determining the type of the instrument inserted into the instrument-inserting channel 102. As shown in FIG. 9A, the bar code reader 2111 is mounted on the outer surface of the instrument-inserting channel 102. A barcode 2501 is printed on the instrument 2500.

When the instrument 2500 is not inserted into the instrument-inserting channel 102 (FIG. 9A), the bar code reader 2111 does not transmits a signal to the system controller 205. When the instrument 2500 is inserted into the instrument-inserting channel 102 (FIG. 9B), the barcode 2501 on the instrument 2500 passes close by the bar code reader 2111. Therefore, when the instrument 2500 is inserted into the instrument-inserting channel 102, the bar code reader 2111 reads the barcode 2501 on the instrument 2500, and transmits a signal carrying code (i.e., a signal indicating the type of the instrument 2500) to the system controller 205. If the barcode 2501 on the instrument 2500 is not located in front of the bar code reader 2111 when the instrument is inserted into the instrument-inserting channel, the bar code reader 2111 can output a signal which indicates that the instrument is inserted into the instrument-inserting channel 102.

With this configuration, the system controller 205 can obtain not only the number of times by which the instrument 2500 is inserted but also the type of the instrument 2500.

FIG. 10 is a flowchart illustrating a procedure for counting the total number of times by which the instrument is inserted into the instrument-inserting channel 102, according to the sixth embodiment of the invention. This procedure includes categorization by the type of the electronic endoscope and the type of the instrument.

A three-element array fA[f1A, f2A, f3A] in FIG. 10 represents the number of times by which the instrument is inserted into the instrument-inserting channel 102 when the electronic endoscopes of type-A is used. A three-element array fB[f1B, f2B, f3B] in FIG. 10 represents the number of times by which the instrument is inserted into the instrument-inserting channel 102 when the electronic endoscopes of type-B is used. A three-element array fC[f1C, f2C, f3C] in FIG. 10 represents the number of times by which the instrument is inserted into the instrument-inserting channel 102 when the other type of the electronic endoscope is used.

Elements "f1A", "f2A" and "f3A" correspond to the number of times of insertions regarding an instrument of type-A, type-B and the other types, respectively. Similarly, elements "f1B", "f2B" and "f3B" correspond to the number of times of insertions regarding an instrument of type-A, type-B and the other types, respectively. Elements "f1C", "f2C" and "f3C" correspond to the number of times of insertions regarding an instrument of type-A, type-B and the other types, respectively.

The procedure shown in FIG. 10 starts when power of the endoscope processor 200 is turned on, and stays in the memory while the endoscope processor 200 is supplied with power. Accordingly, the procedure shown in FIG. 10 is executed while the endoscope processor 200 is operated. Arrays "fA", "fB" and "fC" are stored in the memory 208, and therefore, the arrays are maintained even though the endoscope processor 200 is turned OFF.

In S601, it is determined whether the electronic endoscope 100 is connected to the endoscope processor 200 or not. Step S601 is repeated until the electronic endoscope 100 is connected to the endoscope processor 200. If the electronic endoscope 100 is connected to the endoscope processor 200, control proceeds to S602.

In S602, it is determined whether the electronic endoscope 100 connected to the endoscope processor 200 is type-A or not. If the electronic endoscope 100 connected to the endoscope processor 200 is type-A (S602:YES), control proceeds to S604A.

In S604A, values of elements "f1A", "f2A" and "f3A" are copied to variables "f1", "f2" and "f3", respectively. Next, it is determined whether the instrument is inserted into the instrument-inserting channel 102 based on the signal output by the bar code reader 2111 (S605A).

If the instrument is inserted into the instrument-inserting channel 102 (S605A:YES), control proceeds to S606A. If the instrument is not inserted into the instrument-inserting channel 102 (S605A:NO), control proceeds to S608A.

A subroutine which is called at S606A will be described with referenced to FIG. 11. It should be noted that the system controller 205 can understand the type of the instrument inserted into the instrument-inserting channel 102 based on the signal (code) output by the bar code reader 2111.

In S621, it is determined whether the instrument inserted into the instrument-inserting channel 102 is the instrument of type-A or not. If the instrument inserted into the instrument-inserting channel 102 is the instrument of type-A, control proceeds to S623A. If the instrument inserted into the instrument-inserting channel 102 is not the instrument of type-A, control proceeds to S622.

In S623A, the variable "f1" is incremented by 1. That is, the number of times by which the instrument of type-A is inserted into the instrument-inserting channel 102 when the electronic endoscope of type-A is connected to the endoscope processor 200 is incremented by 1. Next, control returns to the main routine (FIG. 10).

In S622, it is determined whether the instrument inserted into the instrument-inserting channel 102 is the instrument of type-B or not. If the instrument inserted into the instrument-inserting channel 102 is the instrument of type-B, control proceeds to S623B. If the instrument inserted into the instrument-inserting channel 102 is not the instrument of type-B, control proceeds to S623C.

In S623B, the variable "f2" is incremented by 1. That is, the number of times by which the instrument of type-B is inserted into the instrument-inserting channel 102 when the electronic endoscope of type-A is connected to the endoscope processor 200 is incremented by 1. Next, control returns to the main routine (FIG. 10).

In S623C, the variable "f3" is incremented by 1. That is, the number of times by which the other type of the instrument is inserted into the instrument-inserting channel 102 when the electronic endoscope of type-A is connected to the endoscope processor 200 is incremented by 1. Next, control returns to the main routine (FIG. 10).

As shown in FIG. 10, after "f1", "f2" or "f3" is updated in S606A, control proceeds to S607A. In S607A, it is determined whether the instrument is inserted or not. Since the bar code reader 2111 can output the signal which indicates that the instrument is inserted into the instrument-inserting channel, the system controller 205 can determine whether the instrument is inserted into the instrument-inserting channel or not based on the signal output by the bar code reader 2111. If the instrument remains inserted into the instrument-inserting channel 102 (S607A:YES), S607A is repeated. If the instrument is not inserted into the instrument-inserting channel 102 (S607A:NO), i.e., the instrument is pulled out of the instrument-inserting channel 102, control proceeds to S608A.

In S608A, it is determined whether the electronic endoscope 100 is detached from the endoscope processor 200 or not. If the electronic endoscope 100 is not detached (S608A: NO), control returns to S605A. If the electronic endoscope 100 is detached (S608A:YES), control proceeds to S609A. In S609A, values of "f1", "f2" and "f3" are copied to elements "f1A", "f2A" and "f3A", respectively. Next, control proceeds to S610.

If the electronic endoscope 100 connected to the endoscope processor 200 is not type-A (S602:NO), control proceeds to S603 where it is determined whether the electronic endoscope 100 connected to the endoscope processor 200 is type-B or not. If the electronic endoscope 100 connected to the endoscope processor 200 is type-B (S603:YES), control proceeds to S604B.

As in the case of the electronic endoscope of type-A (the steps of S604A–S609A), array fB[f1B, f2B, f3B] which indicates the number of times by which the instrument is inserted into the instrument-inserting channel 102 when the electronic endoscopes of type-B is inserted into the endoscope processor is updated in the steps of S604B–S609B. Next, control proceeds to S610.

If the electronic endoscope 100 connected to the endoscope processor 200 is not type-B (S603:NO), control proceeds to S604C. As in the case of the electronic endoscope of type A (the steps of S604A–S609A), array fC[f1C, f2C, f3C] which indicates the number of times by which the instrument is inserted into the instrument-inserting channel 102 when the other type of the electronic endoscopes is connected to the endoscope processor 200 is updated in the steps of S604C–S609C. Next, control proceeds to S610.

In S610, it is determined whether the time period of a rental use contract is to be renewed or not based on directions input to the endoscope processor 200 by the service person via, for example, the keyboard 600. If the time period of the rental use contract is not to be renewed (S610:NO), control returns to S601. If the time period of the rental use contract is renewed (S610:YES), arrays fA[f1A, f2A, f3A], fB[f1B, f2B, f3B] and fC[f1C, f2C, f3C] are reset to 0 (S611). Next, control returns to S601.

The service person can obtain values of elements of arrays fA, fB and fC in S610 through, for example, the monitor 300.

If the time period of the rental use contract is to be renewed (S610:YES), the rental fee (P6) is calculated according to the following equation:

$$P6 = f1A \times m5A1 + f1B \times m5B1 + f1C \times m5C1 + f2A \times m5A2 + f2B \times m5B2 + f2C \times m5C2 + f3A \times m5A3 + f3B \times m5B3 + f3C \times m5C3 \tag{9}$$

where coefficients m5A1-3, m5B1-3 and m5C1-3 are charges for each insertion of instruments. For example, the coefficient m5A1 represents a charge for each use of the instrument of type-A regarding use of the electronic endoscope of type-A. These coefficients are categorized by the type of the instrument and the type of the electronic endoscope. Table. 1 below shows correspondence among the type of the electronic endoscope, the type of the instrument, and coefficients. The service person charges the user the rental fee P6.

TABLE 1

| THE TYPE OF THE ELECTRONIC ENDOSCOPE | THE TYPE OF THE INSTRUMENT | COEFFICIENT |
|---|---|---|
| A | A | m5A1 |
|   | B | m5A2 |
|   | OTHER TYPES | m5A3 |
| B | A | m5B1 |
|   | B | m5B2 |
|   | OTHER TYPES | m5B3 |
| OTHER TYPES | A | m5C1 |
|   | B | m5C2 |
|   | OTHER TYPES | m5C3 |

It is also possible to calculate a rental fee (P6') according to the number of times by which the instrument is inserted without categorization by the type of the electronic endoscope. In this case, the rental fee (P6') can be calculated according to the following equation:

$$P6' = (f1A + f1B + f1C) \times m51 + (f2A + f2B + f2C) \times m52 + (f3A + f3B + f3C) \times m53 \tag{10}$$

where the coefficient m51 represents a charge for each insertion of the instrument of type-A into the instrument-inserting channel 102, and m51 is common to every kind of the electronic endoscope. The coefficient m52 represents a charge for each insertion of the instrument of type-B into the instrument-inserting channel 102, and m52 is common to every kind of the electronic endoscope. The coefficient m53 represents a charge for each insertion of the other types of the instrument into the instrument-inserting channel 102, and m53 is common to every kind of the electronic endoscope.

Is should be appreciated that by omitting the categorization by the type of the electronic endoscope in FIG. 10, it becomes possible to count the number of times by which the instrument is inserted into the instrument-inserting channel 102 for all types of the electronic endoscope.

Seventh Embodiment

FIG. 12 is a flowchart illustrating a procedure for calculating a rental fee based on both of the time period of use of the electronic endoscope and the number of times by which the still image is captured, according to a seventh embodiment of the invention. It should be noted that an entire configuration of an endoscope system according to the seventh embodiment is substantially the same as the endoscope system 1 (FIG. 1).

This procedure is performed under control of the system controller 205. As in the case of FIG. 4, variables "tA", "tB" and "tC" represent time periods of use regarding the electronic endoscope of type-A, type-B and the other types, respectively. As in the case of FIG. 5, variables "pA", "pB" and "pC" represent the number of times by which the still image is captured using the electronic endoscope of type-A, type-B and the other types, respectively.

The procedure shown in FIG. 12 starts when power of the endoscope processor 200 is turned on, and stays in the memory while the endoscope processor 200 is supplied with power. Accordingly, the procedure shown in FIG. 12 is executed while the endoscope processor 200 is operated. Variables tA, tB, tC, pA, pB and pC are stored in the memory 208, and therefore, these variables are maintained even though the endoscope processor 200 is turned OFF.

In S701, it is determined whether the electronic endoscope 100 is connected to the endoscope processor 200 or not. Step S701 is repeated until the electronic endoscope 100 is connected to the endoscope processor 200. If the electronic endoscope 100 is connected to the endoscope processor 200, control proceeds to S702.

In S702, it is determined whether the electronic endoscope 100 connected to the endoscope processor 200 is type-A or not. If the electronic endoscope 100 connected to the endoscope processor 200 is type-A (S702:YES), control proceeds to S704A.

In S704A, time-information when the electronic endoscope is connected to the endoscope processor 200 is assigned to a variable "t1A". Next, the system controller 205 waits until the signal indicating capture operation of the control switches 109 is input thereto (S705A). If the signal indicating capture operation of the control switches 109 is input to the system controller 205(S705A:YES), i.e., a still image is captured, the variable "pA" is incremented by 1 (S706A).

Next, it is determined whether the electronic endoscope 100 is detached from the endoscope processor 200 or not (S707A). If the electronic endoscope 100 is not detached (S707A:NO), control returns to S705A. If the electronic endoscope 100 is detached (S707A:YES), control proceeds to S708A.

In S708A, time information when the electronic endoscope 100 is detached from the endoscope processor 200 is assigned to a variable "t2A". Next, the time period of use of the electronic endoscope of type-A (tA) is updated according to tA=tA+(t2A−t1A) in S709A.

It should be appreciated that the variable "tA" calculated according to the above equation (tA=tA+(t2A−t1A)) represents a total time period of use of the electronic endoscope of type-A. Next, control proceeds to S710.

If the electronic endoscope 100 connected to the endoscope processor 200 is not type-A (S702:NO), control proceeds to S703 where it is determined whether the electronic endoscope 100 connected to the endoscope processor 200 is type-B or not. If the electronic endoscope 100 connected to the endoscope processor 200 is type-B (S703:YES), control proceeds to S704B.

As in the case of the electronic endoscope of type-A (the steps of S704A–S709A), the number of times by which the still image is captured when the electronic endoscope of type-B is used (pB) is updated according to pB=pB+1, the time period of use of the electronic endoscope of type-B (tB) is updated according to tB=tB+(t2B−t1B) (the steps of S704B–S709B).

If the electronic endoscope 100 connected to the endoscope processor 200 is not type-B (S703:NO), control proceeds to S704C. As in the case of the electronic endoscope of type-A (the steps of S704A–S709A), the number of times by which the still image is captured when the other types of the electronic endoscopes is used (pC) is updated according to pC=pC+1, the time period of use of the other types of electronic endoscope (tC) is updated according to tC=tC+(t2C−t1C) (the steps of S704C–S709C).

In S710, it is determined whether the time period of a rental use contract is to be renewed or not based on directions input to the endoscope processor 200 by the service person via, for example, the keyboard 600. If the time period of the rental use contract is not to be renewed (S710:NO), control returns to S701. If the time period of the rental use contract is renewed(S710:YES), variables tA, tB, tC, pA, pB and pC are reset to 0 (S711). Next, control returns to S701.

The service person can obtain values of tA, tB, tC, pA, pB and pC in S710 through, for example, the monitor 300. If the time period of the rental use contract is to be renewed (S710:YES), the rental fee (P7) is calculated according to the following equation:

$$P7 = (tA \times m6A + tB \times m6B + tC \times m6C) + (pA \times m7A + pB \times m7B + pC \times m7C) \qquad (11)$$

where the coefficients m6A, m6B and m6C represent charges per unit time regarding use of the electronic endoscope of type-A, type-B and the other types, respectively. Coefficients m7A, m7B and m7C represent charges for each capture of a still image using the electronic endoscope of type-A, type-B and the other types, respectively.

As described above, the rental fee (P7) calculated according to the above equation (11) reflects both of the time period of use of the electronic endoscope and the number of times by which the still image is captured. Therefore, if time periods of use of the electronic endoscopes in two cases (in first case, the still image is not captured, and in second case, the still image is captured) are the same, the rental fee in the first case can be lowered in comparison with the second case.

As an alternative to the above equation (11) for calculating P7, it is also possible to calculate a rental fee according to the following equation (12) in which a charge per unit time regarding use of the electronic endoscope increases with increase of the number of times by which the still image is captured.

$$P7' = ((tA \times m6A) \times (1 + pA \times m7A)) + ((tB \times m6B) \times (1 + pB \times m7B)) + ((tC \times m6C) \times (1 + pC \times m7C)) \qquad (12)$$

As can be seen from the above equation (12), if the still image is not captured while the electronic endoscope is connected to the endoscope processor 200, a charge for a time period of use of the electronic endoscope (i.e., tA×m6A, tB×m6B or tC×m6C) is multiplied by 1 (i.e., pA×m7A, pB×m7B and pC×m7C=0). If the still image is captured while the electronic endoscope is connected to the endoscope processor 200, the rental fee P7' increases with increase of the number of times by which the still image is captured.

It should be noted that the various procedures mentioned above with reference to FIG. 2-5, 8, 10-12 may be stored as computer programs in a ROM (not shown) incorporated in the system controller 205.

In the embodiments described above, various kinds, of data including variables, arrays, coefficients, and the like are preferably stored in the memory 208 provided in the endoscope processor 200 and processed by the system controller 205.

Variations of the embodiments described will occur to persons of the art. For example, various kinds of data including variables, arrays, coefficients, and the like may be transmitted to an external device (for example, the computer 800 shown in FIG. 1) that is connected to the endoscope processor through an interface cable. The various kinds of data can be processed on the external device. In this case, rental fees can be calculated on the external device.

As described above, according to embodiments of the present invention, an endoscope system which enables to collect accurate information regarding usage of the endoscope system is accomplished.

The present disclosure relates to the subject matter contained in Japanese Patent Application No. 2001-162090, filed on May 30, 2001, which is expressly incorporated herein by reference in its entirety.

What is claimed is:

1. An electronic endoscope system, comprising:
an electronic endoscope;
an endoscope processor to which said electronic endoscope is detachably connected;
a usage status monitoring system which monitors a usage status of said electronic endoscope system and outputs status data; and
a usage condition obtaining system which obtains a usage condition of said electronic endoscope system based on the status data, said usage condition obtaining system updating the usage condition based on the status data successively output by said usage status monitoring system;
wherein said usage condition obtaining system includes a first memory in which the usage condition is stored;
wherein said usage status monitoring system includes a detecting system which determines whether said endoscope processor is supplied with power, the status data including a detection result of said detecting system; and
wherein said usage condition obtaining system includes a timer, and a time measuring system which measures a total time period for which said endoscope processor is supplied with power using said timer based on the detection result output by said detecting system, the usage condition including the total time period.

2. An electronic endoscope system, comprising:
an electronic endoscope;
an endoscope processor to which said electronic endoscope is detachably connected;
a usage status monitoring system which monitors a usage status of said electronic endoscope system and outputs status data; and
a usage condition obtaining system which obtains a usage condition of said electronic endoscope system based on the status data, said usage condition obtaining system updating the usage condition based on the status data successively output by said usage status monitoring system;
wherein said usage condition obtaining system includes a first memory in which the usage condition is stored;
wherein said electronic endoscope includes an instrument-inserting channel configured to have an instrument inserted therein;
wherein said usage status monitoring system includes a detecting system which determines whether the instrument is inserted into the instrument-inserting channel, the status data including a detection result of said detecting system; and
wherein said usage condition obtaining system includes a counting system which counts the number of times that the instrument is inserted into the instrument-inserting channel based on the detection result output by said detecting system, the usage condition including the number of times that the instrument is inserted into the instrument-inserting channel.

3. The electronic endoscope system according to claim 1, wherein said detecting system includes a mechanical switch provided in said electronic endoscope, a member of said mechanical switch being pressed when the instrument is inserted into the instrument-inserting channel; and
wherein said detecting system determines whether the instrument is inserted into the instrument-inserting channel based on a signal output by said mechanical switch.

4. The electronic endoscope system according to claim 1, wherein said detecting system includes a light-emitting device and a photodetector which are provided in said electronic endoscope, said light-emitting device and said photodetector being placed so that a light beam emitted by said light-emitting device is blocked by the instrument when the instrument is inserted into the instrument-inserting channel; and
wherein said detecting system determines whether the instrument is inserted into the instrument-inserting channel based on a signal output by said photodetector.

5. The electronic endoscope system according to claim 2, wherein said detecting system is configured to detect the type of the instrument inserted into the instrument-inserting channel; and
wherein said counting system categorizes the number of times that the instrument is inserted into the instrument-inserting channel by the type of the instrument.

6. The electronic endoscope system according to claim 5, wherein said detecting system includes a bar code reader provided in said electronic endoscope; and
wherein said bar code reader reads a bar code on the instrument when the instrument is inserted into the instrument-inserting channel, the bar code on the instrument representing the type of the instrument.

7. An electronic endoscope system, comprising:
an electronic endoscope;
an endoscope processor to which said electronic endoscope is detachably connected;
a usage status monitoring system which monitors a usage status of said electronic endoscope system and outputs status data;
a usage condition obtaining system which obtains a usage condition of said electronic endoscope system based on the status data, said usage condition obtaining system updating the usage condition based on the status data successively output by said usage status monitoring system; and
an external device which is connected to said endoscope processor, said external device being configured to input instructions enabling usage, based on renewal of a rental agreement, of the electronic endoscope,
wherein said usage condition obtaining system is incorporated into said external device;
wherein said usage condition obtaining system includes a first memory in which the usage condition is stored;
wherein said endoscope processor includes a light source which emits light for illuminating an object to be observed to a light guide provided in said electronic endoscope;

wherein said usage status monitoring system includes a detecting system which determines whether said light source is energized, the status data including a detection result of said detecting system;

wherein said usage condition obtaining system includes a timer, and a time measuring system which measures a total time period for which said light source is energized using said timer based on the detection result output by said detecting system, the usage condition including the total time period;

wherein said detecting system further determines whether said endoscope processor is supplied with power; and wherein said time measuring system measures a total time period for which said endoscope processor is supplied with power using said timer based on the detection result output by said detecting system, the usage condition including the total time period.

* * * * *